United States Patent [19]

Fung et al.

[11] Patent Number: 4,916,209

[45] Date of Patent: Apr. 10, 1990

[54] BIOABSORBABLE POLYDEPSIPEPTIDE, PREPARATION AND USE THEREOF

[75] Inventors: Fu-Ning Fung, Salem; Raymond C. Glowaky, Niantic, both of Conn.

[73] Assignee: Pfizer Inc., New York, N.Y.

[21] Appl. No.: 137,262

[22] Filed: Dec. 23, 1987

[51] Int. Cl.⁴ .............................................. C08G 69/00
[52] U.S. Cl. ..................... 528/403; 528/271; 528/328; 528/354; 528/361; 528/417
[58] Field of Search ............... 528/403, 328, 271, 354, 528/361, 417

[56] References Cited

U.S. PATENT DOCUMENTS

| | | | |
|---|---|---|---|
| Re. 30,170 | 12/1979 | Goodman et al. ................... | 528/327 |
| 3,773,737 | 11/1973 | Goodman et al. ................. | 260/78 A |
| 4,052,988 | 10/1977 | Doddi et al. ...................... | 128/335.5 |
| 4,209,607 | 6/1980 | Shalaby et al. ..................... | 528/291 |
| 4,343,931 | 8/1982 | Barrows ............................. | 528/291 |
| 4,441,496 | 4/1984 | Shalaby et al. ................... | 128/335.5 |
| 4,653,497 | 3/1987 | Bezwada et al. ................. | 128/335.5 |

OTHER PUBLICATIONS

Rumsh et al., FEBS Letters, 9, 64–66, 1970.
Helder et al., Makromol. Chem., Rapid Commun., 7, 193–198, 1986.
Yonezawa et al., Makromol. Chem., Rapid Commun., 6, 607–611, 1985.

*Primary Examiner*—Harold D. Anderson
*Attorney, Agent, or Firm*—Peter C. Richardson; Lawrence C. Akers; Mark Dryer

[57] ABSTRACT

Novel, semi-crystalline depsipeptide polymers and copolymers particularly suitable for use in fabricating bioabsorbable medical implant devices such as sutures or clips and obtained through ring-opening polymerization of certain 3-substituted-2,5-morpholinediones prepared by reacting a naturally occurring alpha-amino acid with an alpha-halo acid chloride in inert solvent in the presence of an acid acceptor.

8 Claims, 1 Drawing Sheet

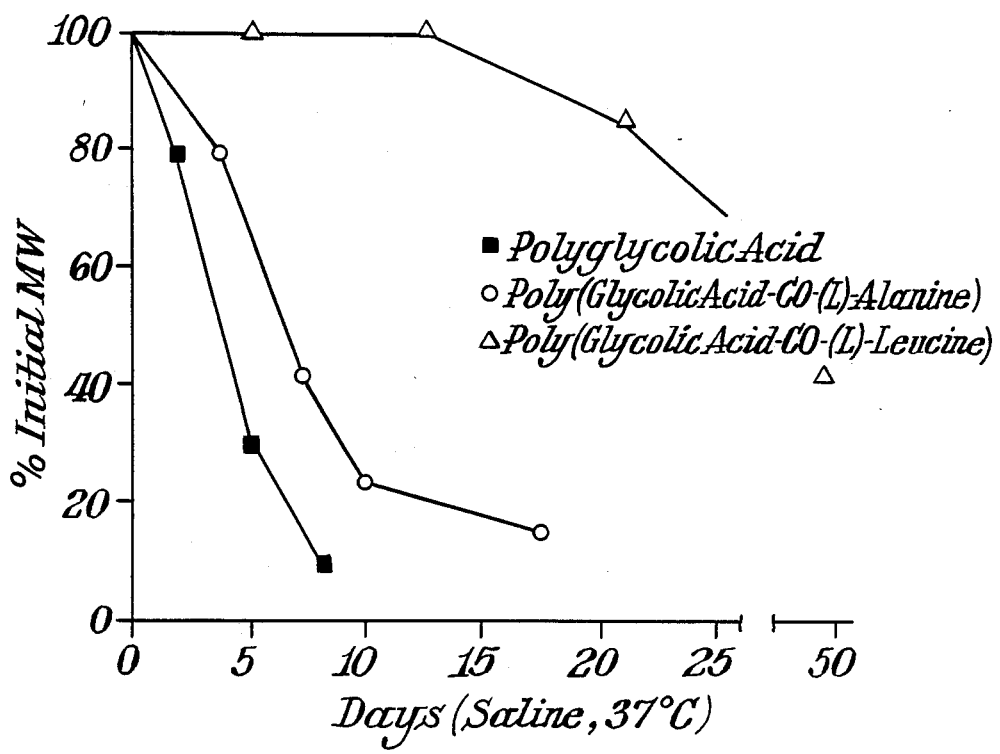

BIOABSORBABLE POLYDEPSIPEPTIDE, PREPARATION AND USE THEREOF

BACKGROUND OF THE INVENTION

This invention concerns certain 3-substituted-2,5-morpholinediones and their polymerization or copolymerization to bioabsorbable depsipeptide polymers which can be fabricated into useful medical implant devices such as sutures.

For the past decade or so, synthetic resorbable sutures have been replacing natural catgut in many applications as biodegradable wound closures since the synthetics, unlike the natural polymers, are consistent and predictable in their strength and sorption properties.

At present, the synthetic suture market is dominated by high molecular weight polyglycolic acid (PGA) and a modified PGA copolymer containing about 10 mole percent lactic acid. Despite their superiority to catgut, however, these resins lack certain desirable properties. For example, they tend to be resorbed too readily, they are too rigid as monofilaments, and they cannot be sterilized by irradiation.

Certain modifications of these resins have been introduced in an attempt to overcome such limitations. For example, U.S. Pat. No. 4,052,988 discloses a poly(p-dioxanone) (PDS) having a structure similar to PGA but purportedly of a lower resorption rate and more readily handled as monofilaments. Such property improvements are also claimed by the modified PGA polymers of U.S. Pat. Nos. 4,209,607 and 4,343,931, which incorporate amide bonding into the polymer chain.

Attempts at preparing resorbable polydepsipeptides include the copolymerization of a racemic N-carboxyanhydride with a racemic anhydrosulfite as disclosed in U.S. Pat. No. 3,773,737. Such a copolymerization, however, produces a heterogeneous product having random and racemic ester/amide groups and is therefore incapable of yielding crystalline polymers. The copolymerization of p-dioxanone with up to 15 mole percent of a 2,5-morpholinedione disclosed in U.S. Pat. No. 4,441,496 was purported to improve the resorption rate of PDS. Recent publications by Helder et al., Makromol. Chem., Rapid Commun., 6, 9–14, 1985, and Yonezawa et al., ibid, 6, 607–611, 1985, have demonstrated the preparation of polydepsipeptides from the ring-opening polymerization of 6-substituted-2,5-morpholinediones.

Despite such developments, the need still exists for a true alternating bioabsorbable polymer of suitable strength and resorption rate which can be readily melt processed. The primary objective of the present invention, therefore, is to satisfy this need.

Preparation of 3-benzyl-2,5-morpholinediones, employed in this invention, by silver oxide catalyzed condensation of N-(bromoacetyl)-L-phenylalanine is reported by Rumsh et al., FEBS Letters, 9, 64, 1970.

SUMMARY OF THE INVENTION

It has now been found that certain optically active 3-substituted-2,5-morpholinediones can be readily prepared by a novel and expeditious procedure, then converted by ring-opening polymerization or copolymerization to semi-crystalline polydepsipeptide compositions of well defined melt temperatures which are particularly suitable for fabrication into bioabsorbable medical devices.

The said novel procedure includes a process for the preparation of a 3-substituted-2,5-morpholinedione having the structural formula I

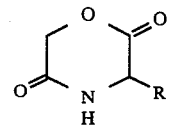

wherein
R=$C_1$-$C_{12}$ alkyl, $C_1$-$C_6$ alkoxy($C_1$-$C_6$ alkyl), aryl, aryl($C_1$-$C_{12}$ alkyl), $C_1$-$C_{12}$ alkylaryl, $C_1$-$C_6$ alkylaryl($C_1$-$C_6$ alkyl), $C_1$-$C_6$ alkylthio($C_1$-$C_6$ alkyl), $C_1$-$C_6$ alkylsulfinyl($C_1$-$C_6$ alkyl), $C_1$-$C_6$ alkylsulfonyl($C_1$-$C_6$ alkyl), cyano($C_1$-$C_{12}$ alkyl) or aminocarbonyl($C_1$-$C_{12}$ alkyl), with each aryl group having up to 10 carbons in the nuclear ring, which comprises the steps of:

(a) contacting an amino acid having the structural formula II

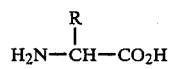

with an alpha-halo acid halide having the structural formula III

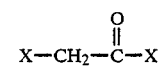

wherein
X=Cl or Br, to form an intermediate having the structural formula IV

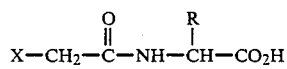

and then
(b) cyclizing the intermediate IV in an inert solvent in the presence of an acid acceptor.

Preferably, in step (a) the amino acid is one in which R=alkyl of from 1 to 4 carbons, benzyl or 2-methylthioethyl, especially (L)-alanine, and the alpha-halo acid is chloroacetyl chloride, while in step (b) the solvent is dimethylformamide and the acid acceptor is triethylamine.

The above-described 3-substituted-2,5-morpholinedione of formula I is a useful intermediate for the preparation of the novel polydepsipeptides of the present invention as hereinafter described.

Thus, according to the present invention there is provided an optically-active, hydrolysable, semi-crystalline polydepsipeptide having a number average molecular weight of from about 5,000 to 200,000 and the structural formula V:

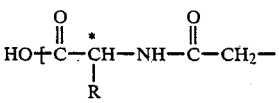

-continued

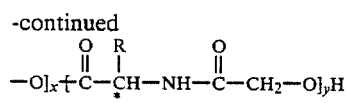

wherein x,y are relative amounts of (D) and (L) optical isomers, respectively, wherein the asterisk indicates the stated optical activity and $x/(x+y)$ is either less than about 0.45 or greater than about 0.55.

Also disclosed but not claimed herein is a depsipeptide copolymer having a molecular weight of from about 5,000 to 200,000 and the structural formula VI:

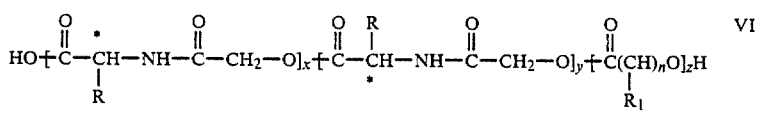

wherein $R_1$ is H or $CH_3$, $z/(x+y+z)$ is from about 0.01 to 0.5, and n is 1 or 5, with the proviso that when n is 5, $R_1$ is H. The polydepsipeptide polymer of formula V is semi-crystalline and hydrolyzable, and a preferred embodiment is a polymer wherein R is an alkyl of from 1 to 4 carbons, benzyl or 2-methylthioethyl, especially wherein the polymer has a number average molecular weight of from about 10,000 to 50,000 with R being $CH_3$ and $x/(x+y)$ being from about 0.2 to 0.4.

The present invention also provides a process for the preparation of the disclosed polydepsipeptide which comprises polymerizing an optically active 3-substituted-2,5-morpholinedione having the structural formula I in the presence of an organometallic catalyst.

The depsipeptide copolymer of formula VI may be prepared by a process which comprises polymerizing 1.0 mole of such a 3-substituted-2,5-morpholinedione with from about 0.02 to 1.0 mole of a cyclic lactone having the structural formula VII or VIII

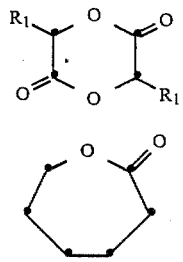

in the presence of a catalyst.

The polymerization or copolymerization is preferably conducted neat at a temperature of from about 100° to 250° C.

The present invention further provides a bioabsorbable surgical device fabricated from the disclosed polydepsipeptide of formula V, preferably in the form of a suture or clip.

BRIEF DESCRIPTION OF THE DRAWING

The above and other objectives, features and advantages of the present invention will be apparent from the following detailed description in conjunction with the accompanying FIGURE, which compares the resorption rates typical of the disclosed polydepsipeptides to that of prior polymer PGA.

DETAILED DESCRIPTION OF THE INVENTION

The novel, semi-crystalline polymers of the present invention are prepared by the catalytic ring-opening polymerization or copolymerization of certain optically active 3-substituted-2,5-morpholinediones of the structural formula I

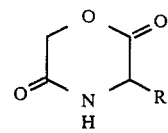

wherein $R = C_1-C_{12}$ alkyl, $C_1-C_6$ alkoxy($C_1-C_6$ alkyl), aryl, aryl($C_1-C_{12}$ alkyl), $C_1-C_{12}$ alkylaryl, $C_1-C_6$ alkylaryl($C_1-C_6$ alkyl), $C_1-C_6$ alkylthio($C_1-C_6$ alkyl), $C_1-C_6$ alkylsulfinyl($C_1-C_6$ alkyl), $C_1-C_6$ alkylsulfonyl($C_1-C_6$ alkyl), cyano($C_1-C_{12}$ alkyl) or aminocarbonyl($C_1-C_{12}$ alkyl), with each aryl group having up to 10 carbons in the nuclear ring, with the comonomer for the copolymerization being a cyclic lactone of the structural formula VII or VIII

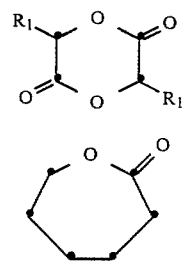

wherein $R_1 =$ H or $CH_3$.

The 3-substituted-2,5-morpholinedione monomers of the present invention, either optically active or inactive, are prepared by a novel process in which an amino acid having the structural formula II

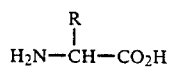

is contacted with an alpha-halo acid halide having the structural formula III

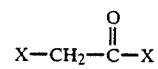

wherein X = chlorine or bromine, to form an intermediate having the structural formula IV

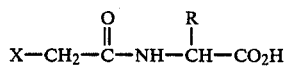

and the intermediate IV is cyclized in an inert solvent in the presence of an acid acceptor.

When an optically active amino acid is used to prepare the 3-substituted-2,5-morpholinedione monomer, the optical activity is retained in the monomer, and also in the derived polymer. Thus, (L)-alanine gives (L)-3-methyl-2,5-morpholinedione which, upon polymerization, yields poly(glycolic acid-co-(L)-alanine). This optically active polymer is semi-crystalline with a melting transition of 232° C. and a specific rotation of −67.8° (C=1, DMSO). The polymer's semi-crystallinity results in fabricated devices such as sutures and clips with physical/mechanical and resorption properties superior to those realized with racemic polymer.

$x/(x+y)$=either less than about 0.45 or greater than about 0.55, or copolymerized with from about 0.02 to 1.0 mole, preferably from about 0.1 to 0.4 mole, of a cyclic lactone of the structural formula VII or VIII

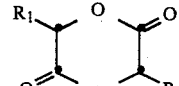

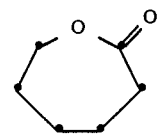

to yield a copolymer of the structural formula VI

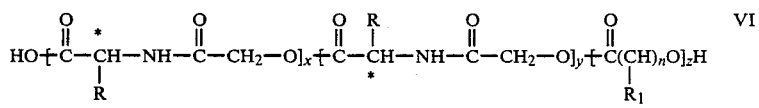

wherein
$z/(x+y+z)$=from about 0.01 to 0.5, preferably 0.05 to 0.20, and
$n=1$ or 5,
with the proviso that when $n=5$, $R_1=H$.

While any amino acid of the general formula II can be used for preparing the intermediate IV, preferred are the amino acids shown in Table I. This table indicates the common name of the amino acid, the structural formula, and the radical or substituent group R, the group R being that portion of the amino acid appearing as the appendage in the subsequent polymerization or copolymerization. Of these amino acids, (L)-leucine and (L)-alanine are especially preferred.

The amino acid and alpha-halo chloride are preferably contacted in basic aqueous medium at a temperature of from about −5 to +25° C., the resulting intermediate IV being simultaneously extracted from the reaction medium into an inert, water-immiscible solvent such as ethyl ether. Intermediate IV is then isolated by evaporation of the solvent extract and used directly in the subsequent cyclization, although its purification before use, such as by recrystallization from ethyl acetate, may be employed.

The intermediate IV is then cyclized in an inert solvent in the presence of an acid acceptor. While any solvent nonreactive to intermediate IV or the acid acceptor may be used, dimethylformamide is preferred. The cyclization will normally be conducted at a temperature of from about 25° to 200° C., preferably about 75° to 125° C., and will require from about 0.5 to 20 hours, usually about 6 to 12 hours.

An optically active form of the prepared 3-substituted-2,5-morpholinedione is then either polymerized to a polymer of the structural formula V

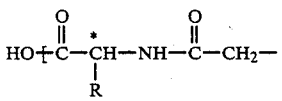

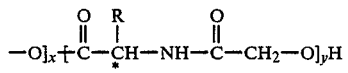

wherein
x,y=relative amounts of (D) and (L) optical isomers and

TABLE I

| Name | Formula II Amino Acids Formula | R |
|---|---|---|
| (L)-alanine | CH₃CHCOOH \| NH₂ | CH₃ |
| (L)-isoleucine | CH₃CH₂CH(CH₃)CHCOOH \| NH₂ | CH(CH₃)CH₂CH₃ |
| (L)-leucine | (CH₃)₂CHCH₂CHCOOH \| NH₂ | CH₂CH(CH₃)₂ |
| (L)-methionine | CH₃SCH₂CH₂CHCOOH \| NH₂ | CH₂CH₂SCH₃ |
| (L)-phenyl-alanine | C₆H₅CH₂CHCOOH \| NH₂ | CH₂C₆H₅ |
| (L)-valine | (CH₃)₂CHCHCOOH \| NH₂ | CH(CH₃)₂ |

By optically active 3-substituted-2,5-morpholinedione monomer is meant such a monomer with an optical purity of greater than 50 percent. This optical purity is expressed as the percent of an optically pure isomer in a mixture of the isomer with its enantiomorph. Thus, an optically active (L)-3-methyl-2,5-morpholinedione of 80 percent optical purity would consist of 80 percent optically pure (L)-3-methyl-2,5-morpholinedione and 20 percent optically pure (D)-3-methyl-2,5-morpholinedione. Such a composition can be realized, for example, by blending 60 parts (L)-3-methyl-2,5-morpholinedione and 40 parts (D,L)-3-methyl-2,5-morpholinedione, prepared as indicated hereinbefore from (L)-alanine and (D,L)-alanine, respectively. Optically active monomers with an optical purity of from about 55 to 100 percent (L) or (D), especially 60 to 80 percent (L), are preferred.

The polymerization, or copolymerization, is conducted, either neat (without solvent) or in an inert solvent, in the presence of an organometallic catalyst. Preferably, the polymerization is conducted neat. In this case, the temperature of polymerization will depend on the melting point of the intermediate IV, since the reaction mixture must be in a molten state. The polymerization is therefore normally carried out above about 120° C., and preferably between about 150° and 250° C., higher temperatures resulting in excessive decomposition of the product polymer. Under such temperature conditions, the polymerization will normally require from 1 to 10 hours. Solvent polymerization employs similar conditions, suitable inert solvents including such as dimethylformamide, dimethyl sulfoxide and dodecanol.

Any lactone polymerization catalyst may be used for the polymerization. Such catalysts include, for example, zirconium acetoacetonate, stannous chloride and especially stannous octoate.

The resulting polymers and copolymers preferably are semi-crystalline, showing a defined melt temperature, and are bioabsorble to safe by-products, the resorption rate of the polymer being dependent on the nature of the R radical. Such properties make these polymers highly suitable for use in fabricating bioabsorbable medical devices such as sutures and clips.

The following examples are merely illustrative and should not be construed as limiting the present invention, the scope of which is defined by the appended claimes.

EXAMPLE 1

(L)-3-Methyl-2,5-morpholinedione

Into a 5-liter, 4-neck, round-bottom flask equipped with a mechanical stirrer, pH probe, thermometer, two 1-liter addition funnels and a nitrogen bubbler were charged 157 g (3.93 mole) of sodium hydroxide and 1800 ml of water followed by 350 g (3.93 mole) of L-alanine. After all the solids dissolved, 600 ml of diethyl ether was added and solutions of chloroacetyl chloride (500 g, 4.43 mole) in 600 ml of diethyl ether and dilute sodium Hydroxide (225 g in 500 ml water) were added concomitantly while maintaining the pH at about 11 and the temperature at about 0° C. by external cooling. The resulting mixture was allowed to warm to room temperature, and the ether layer separated. The aqueous layer was acidified with concentrated hydrochloric acid to pH 1 and extracted with four 1-liter portions of ethyl acetate. The combined organic extract was dried over anhydrous magnesium sulfate and rotoevaporated to yield 550 g (85%) of 2-chloroacetyl-(L)-alanine as a white crystalline solid, melting point (mp) 93°–96° C. This material can be purified by recrystallization from ethyl acetate, but this is not necessary for the next step.

A total of 404 g (2.44 mole) of the 2-chloroacetyl-(L)-alanine was dissolved in 8 liters of dimethylformamide in a 12-liter round-bottom flask. With stirring, 250 g (2.47 mole) of triethylamine was added and the resulting solution was heated to and maintained at 100° C. for 6 hours. Upon cooling, some solid triethylamine hydrochloride salt crystallized out. This side product was filtered off, and the filtrate was concentrated on a rotoevaporator to give a mixture of (L)-3-methyl-2,5-morpholinedione and triethylamine hydrochloride. The desired product was isolated by adding 530 ml of chloroform to the mixture, filtering the resulting slurry, solvent stripping the filtrate, and finally recrystallizing the residue from isopropanol. This yielded 157 g (50%) of (L)-3-methyl-2,5-morpholinedione having the following characteristics:

mp=153.5°–154.5° C.
$[\alpha]_D = -102°$ (c=2, acetone)
elemental analysis: calc. for $C_5H_7NO_3$: C, 46.49; H, 5.47; N, 10.85%; found: C, 46.58, H, 5.23; N, 10.75%.

Purification of the crude (L)-3-methyl-2,5-morpholinedione may also be accomplished by sublimation.

EXAMPLE 2

(D,L)-3-Methyl-2,5-morpholinedione

This monomer was prepared as described in Example 1, but with (D,L)-alanine rather than (L)-alanine as starting material. The product had a melting point of 137.5°–138.5° C.

EXAMPLE 3

(L)-3-Isobutyl-2,5-morpholinedione

This monomer was prepared as described in Example 1 but with 515 g (3.93 mole) (L)-leucine as starting material. The product had the following characteristics:

mp=127°–128° C.
$[\alpha]_D = -6.6°$ (c=2, acetone)
elemental analysis: calc. for $C_8H_{13}NO_3$: C, 56.11; H, 7.66; N, 8.18%; found: C, 56.08; H, 7.62; N, 8.14%.

EXAMPLE 4

(L)-3-Phenylmethyl-2,5-morpholinedione

This monomer was prepared as described in Example 1, but with 649 g (3.93 mole) (L)-phenylalanine as starting material. The product had the following characteristics:

mp=145°–146° C.
$[\alpha]_D = -11.3°$ (c=2, acetone)
elemental analysis: calc. for $C_{11}H_{11}NO_3$: C, 64.38; H, 5.40; N, 6.83%; found: C, 64.14; H, 5.46; N, 6.73%.

EXAMPLE 5

Poly(glycolic acid-co-(L)-alanine)

Into a flame-dried polymerization tube was charged 10.0 g of the (L)-3-methyl-2,5-morpholinedione prepared in Example 1 and 0.01 g of stannous octoate as catalyst. The tube was evacuated, then flushed with dry nitrogen gas several times and finally sealed under vacuum. The polymerization tube was placed in a 180° C. oil bath for 2 hours. The resulting orange-colored polymer plug was dissolved in 50 ml of hexafluoroisopropanol (HFIP). The HFIP solution was added to 3 liters of acetone with agitation, and the resulting solids were filtered and air dried at room temperature to yield 5.47 g (55%) of poly(glycolic acid-co-(L)-alanine) as a powder. The semi-crystalline polymer had the following characteristics:

$T_m$(mp)=232° C. (DSC measurement)
$\eta$inh=0.61 (50 mg/dL dichloroacetic acid)
$[\alpha]_D = -67.8°$ (c=2, DMSO)

Racemic 3-methyl-2,5-morpholinedione prepared in Example 2 was polymerized to poly(glycolic acid-co-(D,L)-alanine) in similar fashion using zirconium acetoacetonate as catalyst. The polymer, isolated in 60% yield, was amorphous and showed no $T_m$ by DSC analysis.

EXAMPLE 6

Relationship of Monomer Enantiomeric Composition to Polymer Crystallinity and Melt Temperature A mixture consisting of various ratios of (L)-3-methyl-2,5-morpholinedione (A) prepared by Example 1 and (DL)-3-methyl-2,5-morpholinedione (B) prepared in Example 2 were polymerized by the method of Example 5 to give polymers of different melting temperatures (Tm) as shown in Table II.

TABLE II

| A:B | Monomer % (L) | % (D) | $[\alpha]_D$[1] | Polymer $T_m$, °C.[2] |
|---|---|---|---|---|
| 100:0 | 100 | 0 | −102 | 232 |
| 60:40 | 80 | 20 | −61.2 | 203 |
| 50:50 | 75 | 25 | −51.0 | 190 |
| 40:60 | 70 | 30 | −40.8 | 168 |
| 30:70 | 65 | 35 | −30.6 | 152 |
| 20:80 | 60 | 40 | −20.0 | 140 |
| 0:100 | 50 | 50 | 0 | amorphous |

[1] C = 2, acetone
[2] DSC

EXAMPLE 7

Poly(glycolic acid-co-(L)-leucine)

(L)-3-Isobutyl-2,5-morpholinedione prepared in Example 3 was polymerized by the method of Example 5 to give semi-crystalline poly(glycolic acid-co-(L)-leucine) in 58% yield and with the following characteristics:

$\eta$inh=0.77 (50 mg/dL dichloroacetic acid)
$[\alpha]_D = -39.8°$ (c=2, DMSO)

EXAMPLE 8

Poly(glycolic acid-co-(L)-phenylalanine)

(L)-3-Phenylmethyl-2,5-morpholinedione prepared in Example 4 was polymerized by the method of Example 5 to give a semi-crystalline poly(glycolic acid-co-(L)-phenylalanine) in 65% yield with an $[\alpha]_D = -2.05°$ (c=2, DMSO).

EXAMPLE 9

Copolymerization of (L)-3-Isobutyl-3,5-morpholinedione and Glycolide

A mixture of 9 g of (L)-3-isobutyl-3,5-morpholinedione and 1 g of glycolide was polmerized by the method of Example 5. The resulting semi-crystalline copolymer was isolated in 72% yield and had the following characteristics:

$T_m$=114° C. (DSC)
$\eta$inh=0.69 (50 mg/dL, dichloroacetic acid)
$[\alpha]_D = -27.1°$ (c=2, DMSO)

EXAMPLE 10

Melt-spinning of Poly(glycolic acid-co-(L)-luecine)

The polymer prepared in Example 7 was dried in a vacuum over overnight (55° C., 0.05 mm Hg) and then placed in a small scale laboratory melt-spinner at 150° C. to produce strands of fiber with an average diameter about 0.07 mm. Straight pull tensile strength of as-spun fiber was 12,000 psi, which increased to 26,000 psi after drawing to 2.5 times its original length at 85° C.

EXAMPLE 11

Melt-spinning of Poly(glycolic acid-co-alanine)

A polymer ($T_m$=155° C.) prepared as in Example 6 from a 30:70 mixture of (L)- and (DL)-3-methyl-2,5-morpholinedione was dried and spun into a fiber at 160° C. The fiber had a tensile strength of about 12,000 to 20,000 psi.

EXAMPLE 12

Measurement of Relative Resorption Rates

Relative resorption rates of selected polymers were measured by monitoring the decrease in molecular weight with time in 1N aqueous saline solution at 37° C. Samples of the polymers were fabricated by melt pressing a given polymer at the appropriate temperature to produce a clear 20 mil (0.8 mm) film. The film (5 cm squares) was submerged in the saline solution and the molecular weight of the saline incubated sample was measured by size exclusion chromatography as a function of time.

The comparative results, shown in the accompanying FIGURE, indicate that the polydepsipeptides hydrolyze with time, and that the resorption rates can be controlled and varied by choice of polymer type. Thus, the poly(glycolic acid-co-(L)-alanine) of Example 5 shows a rate slightly slower than polyglycolic acid (PGA), a common resorbable suture material. In contrast, the poly(glycolic acid-co-(L)-leucine) of Example 7 shows a rate considerably slower than PGA.

EXAMPLE 13

The procedure of Example 1 is repeated except that D-alanine is substituted for L-alanine in the preparation. The resulting (D)-3-methyl-2,5-morpholinedione is then polymerized by the procedure of Example 5 to yield semi-crystalline poly(glycolic acid-co-(D)-alanine).

I claim:

1. An optically-active, hydrolyzable, semi-crystalline polydepsipeptide having a number average molecular weight of from about 5,000 to 200,000 and the structural formula V:

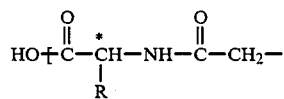

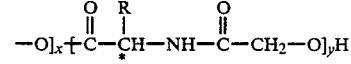

wherein
R is $C_1$-$C_{12}$ alkyl, $C_1$-$C_6$ alkoxy ($C_1$-$C_6$ alkyl), aryl, aryl($C_1$-$C_{12}$ alkyl), $C_1$-$C_{12}$ alkylaryl, $C_1$-$C_6$ alkylaryl($C_1$-$C_6$ alkyl), $C_1$-$C_6$ alkylthio($C_1$-$C_6$ alkyl), $C_1$-$C_6$ alkylsulfinyl($C_1$-$C_6$ alkyl), $C_1$-$C_6$ alkylsulfonyl($C_1$-$C_6$ alkyl), cyano($C_1$-$C_{12}$ alkyl) or aminocarbonyl($C_1$-$C_{12}$ alkyl), with each aryl group having up to 10 carbons in the nuclear ring, p1 x,y are relative amounts of (D) and (L) optical isomers, respectively, wherein the asterisk indicates the stated optical activity, and
the ratio x/(x+y) is either less than about 0.45 or greater than about 0.55.

2. The polydepsipeptide of claim 1 wherein R is alkyl of from 1 to 4 carbons, benzyl or 2-methylthioethyl.

3. The polydepsipeptide of claim 2 wherein the molecular weight is from about 10,000 to 50,000, R is $CH_3$ and $x/(x+y)$ is from about 0.2 to 0.4 or from about 0.6 to 0.8.

4. A bioabsorbable surgical device fabricated from the polydepsipeptide of claim 1.

5. The surgical device of claim 4 in the form of a suture or clip.

6. A process for the preparation of an optically-active, hydrolyzable, semi-crystalline polydepsipeptide according to claim 1, which comprises polymerizing an optically active 3-substituted-2,5-morpholinedione having the structural formula I

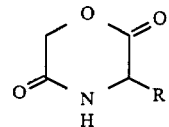

wherein R is as defined in claim 4, in the presence of an organometallic catalyst.

7. The process of claim 6 wherein the polymerization is conducted neat at a temperature of from about 100° to 250° C.

8. A process according to claim 6, wherein the organometallic catalyst is stannous octoate.

* * * * *